(12) United States Patent
Okumura

(10) Patent No.: US 11,045,158 B2
(45) Date of Patent: Jun. 29, 2021

(54) MOBILE X-RAY IMAGING APPARATUS

(71) Applicant: Shimadzu Corporation, Kyoto (JP)

(72) Inventor: Hiroshi Okumura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/644,610

(22) PCT Filed: Oct. 25, 2017

(86) PCT No.: PCT/JP2017/038494
§ 371 (c)(1),
(2) Date: Mar. 5, 2020

(87) PCT Pub. No.: WO2019/082299
PCT Pub. Date: May 2, 2019

(65) Prior Publication Data
US 2020/0330060 A1  Oct. 22, 2020

(51) Int. Cl.
*A61B 6/14* (2006.01)
*A61B 6/00* (2006.01)
*A61B 6/06* (2006.01)

(52) U.S. Cl.
CPC .......... *A61B 6/4405* (2013.01); *A61B 6/06* (2013.01); *A61B 6/461* (2013.01); *A61B 6/56* (2013.01); *A61B 2562/0219* (2013.01)

(58) Field of Classification Search
CPC .......... A61N 2005/1061; A61N 5/1045; G01T 1/175; G01T 1/00; A61B 6/4476; A61B 6/00; A61B 6/4405; A61B 6/4429; A61B 6/4458; G01N 2201/00; G01N 2201/0813; G01N 2223/05
See application file for complete search history.

(56) References Cited

U.S. PATENT DOCUMENTS

2015/0276944 A1 * 10/2015 Enomoto ............... G01T 1/175
378/101

FOREIGN PATENT DOCUMENTS

JP    2006-239070 A    9/2006
JP    2016-043153 A    4/2016

OTHER PUBLICATIONS

Written Opinion by the International Search Authority for PCT application PCT/JP2017/038494, dated Jan. 23, 2018, submitted with a machine translation.

* cited by examiner

*Primary Examiner* — Don K Wong
(74) *Attorney, Agent, or Firm* — Muir Patent Law, PLLC

(57) ABSTRACT

When a control unit 30 detects that the apparatus becomes a traveling mode, the control unit 30 stops the power supply from a power supply circuit 52 to an opening-degree sensor S2 of a collimator leaf and a distance sensor S3 for detecting the distance between an X-ray tube 11 and a subject. On the other hand, for an acceleration sensor S1 for measuring the acceleration of a collimator 12, power supply from the power supply circuit 52 is stopped. When the control unit 30 determines that the apparatus is not in the traveling mode, electric power is supplied to all of the acceleration sensor S1, the opening-degree sensor S2, and the distance sensor S3. As a result, power consumption can be reduced by constantly supplying electric power to the acceleration sensor S1 required to perform constant monitoring, and in the traveling mode, power supply to the opening-degree sensor S2 and the distance sensor S3 used when performing X-ray imaging is stopped, so that power consumption can be reduced.

8 Claims, 4 Drawing Sheets

MOBILE X-RAY IMAGING APPARATUS

TECHNICAL FIELD

The present invention relates to a mobile X-ray imaging apparatus, such as, e.g., an X-ray imaging apparatus of a round type.

BACKGROUND OF THE INVENTION

An X-ray imaging apparatus for rounds for performing X-ray imaging by traveling between hospital rooms is provided with: an X-ray tube for emitting X-rays to a subject; a collimator for restricting the irradiation field of X-rays emitted from the X-ray tube to the subject; a carriage having wheels; a support mechanism provided to the carriage for supporting the X-ray tube and the collimator; and a battery mounted in the carriage. The X-ray imaging apparatus is configured to travel between hospital rooms by electric power by driving a motor mounted on the carriage. In such as a mobile X-ray imaging apparatus, such as, e.g., an X-ray imaging apparatus for rounds, it is preferable to reduce the power consumption of the battery so that X-ray imaging can be performed a greater number of times.

Patent Document 1 discloses an X-ray imaging apparatus for rounds configured to reduce the power consumption of the battery. The X-ray imaging apparatus is configured to electrically connect a storage battery and a dosimeter when an operation command for preparing imaging is output from a controller based on an input operation from an imaging preparation switch and to electrically disconnect them by a selector switch in the case other than the above.

Further, Patent Document 2 discloses a radiographic imaging system in which the power consuming mode of an apparatus can be switched between an imaging capable mode and a power saving mode.

PRIOR ART DOCUMENT

Patent Document

Patent Document 1: Japanese Unexamined Patent Application Publication No. 2006-239070
Patent Document 2: Japanese Unexamined Patent Application Publication No. 2016-43153

SUMMARY OF THE INVENTION

Problems to be Solved by the Invention

In a mobile X-ray imaging apparatus, conventionally, during the traveling of the apparatus that does not perform X-ray imaging, the power supply to the collimator used when performing X-ray imaging is stopped. On the other hand, in recent years, various sensors have been mounted on a collimator for the purpose of grasping the apparatus state in more detail. For example, in addition to a conventional opening-degree sensor for detecting the opening-degree of a collimator leaf provided in a collimator and a distance sensor for detecting the distance between an X-ray tube and a subject, it is conceivable to provide an acceleration sensor in a collimator to measure the impact caused on the collimator during the traveling by this acceleration sensor.

In such a case, when the power supply to the collimator is stopped during the traveling of the apparatus, it becomes unable to measure the acceleration by the acceleration sensor during the traveling. On the other hand, if electric power is supplied to the collimator in order to enable measurements by the acceleration sensor even during the traveling, electric power is consumed by sensors other than the acceleration sensor in the collimator, resulting in large power consumption of the apparatus.

The present invention has been made to solve the above-mentioned problems, and an object of the present invention is to provide a mobile X-ray imaging apparatus capable of preventing unnecessary consumption of electric power by selectively performing power supply to sensors provided in a collimator to supply electric power to a sensor required to perform constant monitoring and supply electric power to other sensors only when necessary.

Means for Solving the Problem

According to the invention as recited in claim 1, a mobile X-ray imaging apparatus equipped with an X-ray tube for emitting X-rays to a subject, a collimator for limiting an irradiation field of X-rays emitted from the X-ray tube to the subject, a carriage having wheels, a support mechanism mounted on the carriage for supporting the X-ray tube and the collimator, and a battery mounted on the carriage. The mobile X-ray imaging apparatus includes:

a plurality of sensors provided in the collimator, a control board provided with a power supply circuit capable of individually supplying electric power to the plurality of sensors and a control circuit for instructing power supply and power supply stop from the power supply circuit to the plurality of sensors, and mounted on the control board; and a control unit mounted on the carriage to control power supply to the plurality of sensors by transmitting a control signal to the control circuit in the control board.

According to the invention as recited in claim 2, the mobile X-ray imaging apparatus as recited in claim 1, further includes:

a traveling mode detection means configured to detect whether or not the apparatus is in a traveling mode for traveling the carriage, wherein the control unit switches a power supply state to the plurality of sensors based on a detection result of the traveling mode detection means.

According to the invention as recited in claim 3, in the mobile X-ray imaging apparatus as recited in claim 2, the traveling mode detection means detects that the apparatus is in the traveling mode by detecting that the support mechanism is positioned at a fixed position which is a position to be placed when the carriage is traveled.

According to the invention as recited in claim 4, in the mobile X-ray imaging apparatus as recited in claim 2, the plurality of sensors includes an opening-degree sensor for detecting an opening-degree of a collimator leaf in the collimator, a distance sensor for detecting an imaging distance between the X-ray tube and the subject and an acceleration sensor for detecting acceleration of the collimator, and the control unit is configured to supply power to the opening-degree sensor, the distance sensor, and the acceleration sensor from the power supply circuit when the carriage is not in the traveling mode and supply power to the acceleration sensor from the power supply circuit when the carriage is in the traveling mode.

According to the invention as recited in claim 5, the mobile X-ray imaging apparatus as recited in claim 1 further includes a digital imaging mechanism including an X-ray detector for imaging an X-ray image by detecting X-rays emitted from the X-ray tube and passed through the subject and a display unit for displaying the X-ray image captured by the X-ray detector. The control unit switches a power supply state to the plurality of sensors based on whether or not the digital imaging mechanism has become an imaging mode.

According to the invention as recited in claim 6, in the mobile X-ray imaging apparatus as recited in claim 5, the plurality of sensors includes an opening-degree sensor for detecting an opening-degree of a collimator leaf in the collimator, a distance sensor for detecting an imaging distance between the X-ray tube and the subject, and an acceleration sensor for detecting acceleration of the collimator, and the control unit supplies electric power from the power supply circuit to the opening-degree sensor, the distance sensor, and the acceleration sensor when the digital imaging mechanism is in the imaging mode and supplies electric power from the power supply circuit to the acceleration sensor when the digital imaging mechanism is not in the imaging mode.

According to the invention as recited in claim 7, the mobile X-ray imaging apparatus as recited in any one of claims 1 to 6 further includes a timer configured to measure a time since power supply to the plurality of sensors from the power supply circuit is initiated, and the control unit acquires detection values of the sensors after the timer measures that a set time has elapsed since electric power supply to the plurality of sensors stabilized.

According to the invention as recited in claim 8, the mobile X-ray imaging apparatus as recited in any one of claims 1 to 6 further includes a stability determination unit configured to determine whether or not electric power supplied from the power supply circuit to the plurality of sensors has become stable. The control unit acquires detection values of the sensors after electric power supplied to the plurality of sensors has stabilized.

Effects of the Invention

According to the invention as recited in claim 1, by selectively performing the power supply to the sensor provided in the collimator by transmitting a control signal to the control circuit from the control unit to supply electric power to a sensor required to perform continuous monitoring and supply electric power to the other sensors only when required, unnecessary power consumption can be prevented.

According to the invention as recited in claim 2, the power supply to each sensor provided in the collimator can be switched between a traveling mode in which no X-ray imaging is performed and a mode other than the traveling mode in which X-ray imaging is performed.

According to the invention as recited in claim 3, it becomes possible to easily recognize that the apparatus is in a traveling mode with a simple configuration.

According to the invention as recited in claim 4, power consumption can be reduced since electric power is constantly supplied to an acceleration sensor required to perform constant monitoring and power supply to an opening-degree sensor and a distance sensor used when performing X-ray imaging is stopped in a traveling mode.

According to the invention as recited in claim 5, it becomes possible to switch the power supply to the respective sensors provided in a collimator between an imaging mode for performing X-ray imaging and a mode other than the imaging mode in which X-ray imaging is not performed.

According to the invention as recited in claim 6, it becomes possible to reduce power consumption since power is constantly supplied to an acceleration sensor required to perform constant monitoring and power supply to an opening-degree sensor and a distance sensor used when performing X-ray imaging is stopped in a mode other than the imaging mode in which X-ray imaging is not performed.

According to the invention as recited in claim 7, it becomes possible to prevent the acquisition of incorrect detection values prior to stabilization of sensor outputs since detection values of sensors are acquired after a predetermined time has elapsed since power supply to the sensors is initiated.

According to the invention as recited in claim 8, it becomes possible to prevent incorrect detection values from being acquired prior to stabilization of power since detection values of sensors are acquired after power supply to the sensors has stabilized.

EMBODIMENTS FOR CARRYING OUT THE INVENTION

Figure 1:
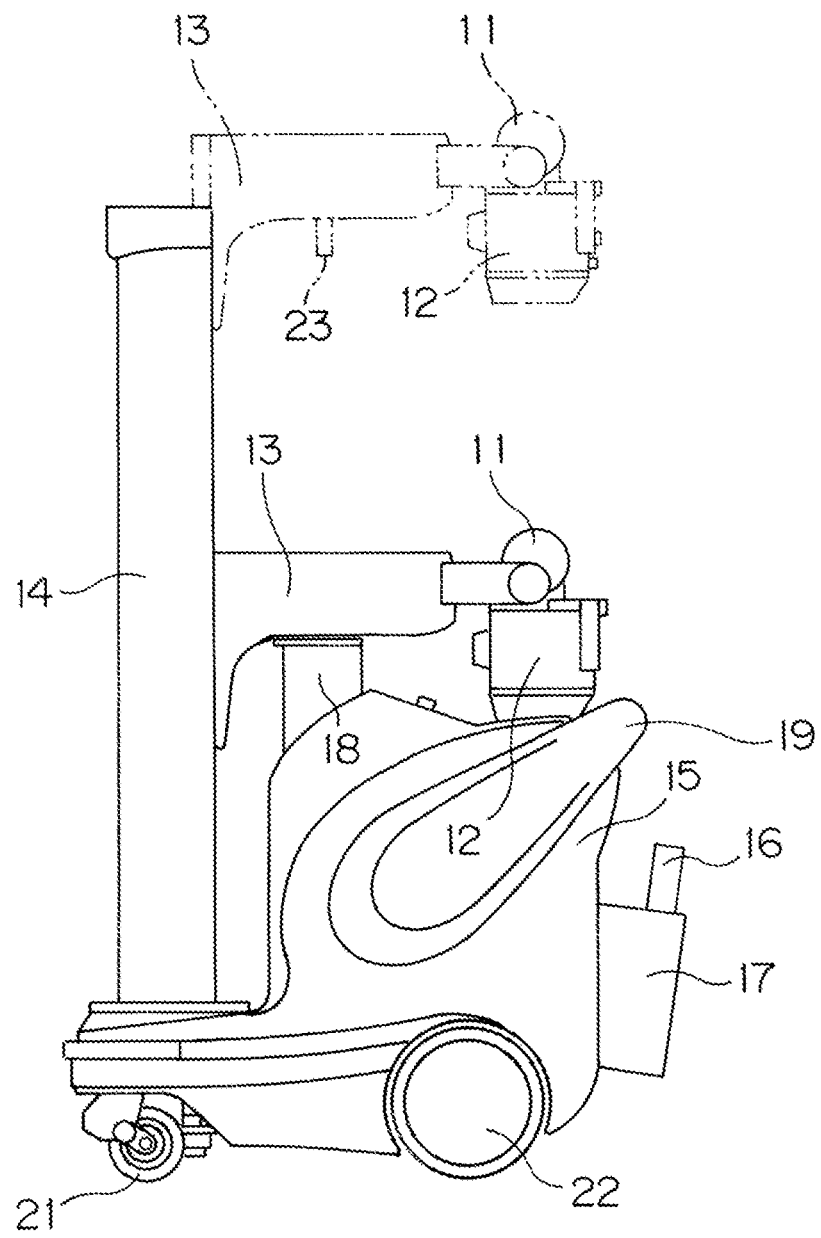
FIG. 1 is a schematic side view of a mobile X-ray imaging apparatus according to a first embodiment of the present invention.
Figure 2:
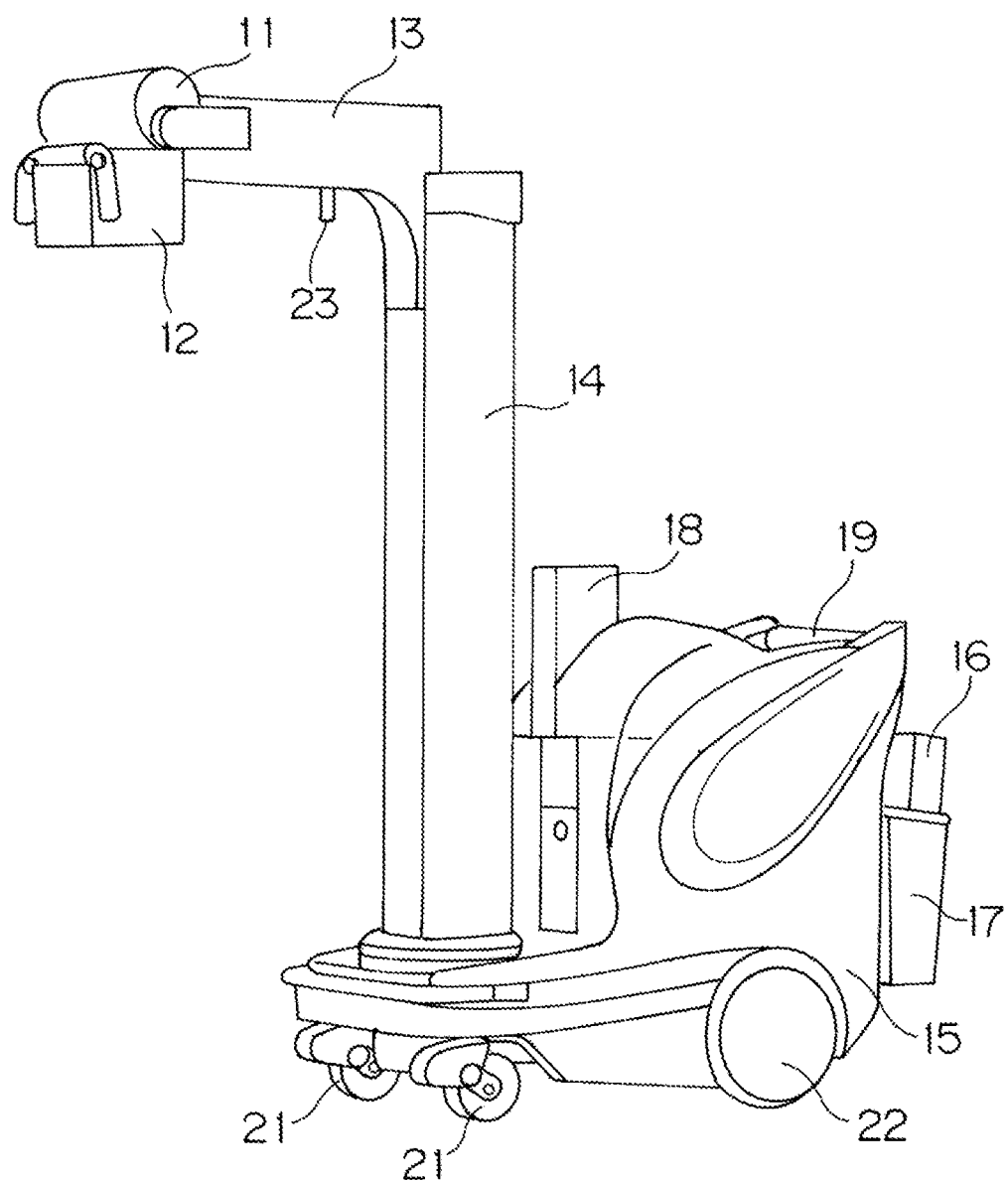
FIG. 2 is a perspective view of the mobile X-ray imaging apparatus according to the first embodiment of the present invention.

Hereinafter, an embodiment of the present invention will be described with reference to the attached drawings. FIG. 1 is a schematic side view of a mobile X-ray imaging apparatus according to the present invention. FIG. 2 is a perspective view of the mobile X-ray imaging apparatus according to the present invention.

The mobile X-ray imaging apparatus is provided with a support post 14 mounted on a carriage 15, an arm 13 provided to the support post 14 in a vertically movable manner, an X-ray tube 11 provided at the tip of the arm 13, a collimator 12 provided below the X-ray tube 11, an X-ray detector 16 for detecting X-rays emitted from the X-ray tube 11 and passed through a subject, and a storage portion 17 for storing the X-ray detector 16. The support post 14 and the arm 13 constitute a support mechanism for supporting the X-ray tube 11 and the collimator 12. The mobile X-ray imaging apparatus is further provided with a pair of left and right front wheels 21, which are wheels for changing a direction, a pair of left and right rear wheels 22, which are wheels for driving, and an operation handle 19 for operating the traveling direction of the carriage 15.

The arm 13 can move up and down between a fixed position, which is a position where the arm 13 is to be placed when traveling the carriage 15, and an imaging position raised from the fixed position, which is indicated by a solid line in FIG. 1. In a state in which the arm 13 in the fixed position, the underside of the arm 13 abuts a fixed portion 18 called an arm catch. In this situation, a pin 23 provided on the lower surface of the arm 13 is received in a hole (not shown) formed in the fixed portion 18. As shown in FIG. 2, the arm 13 pivots about the support post 14 in a state in which it is raised from the fixed position.

Figure 3:
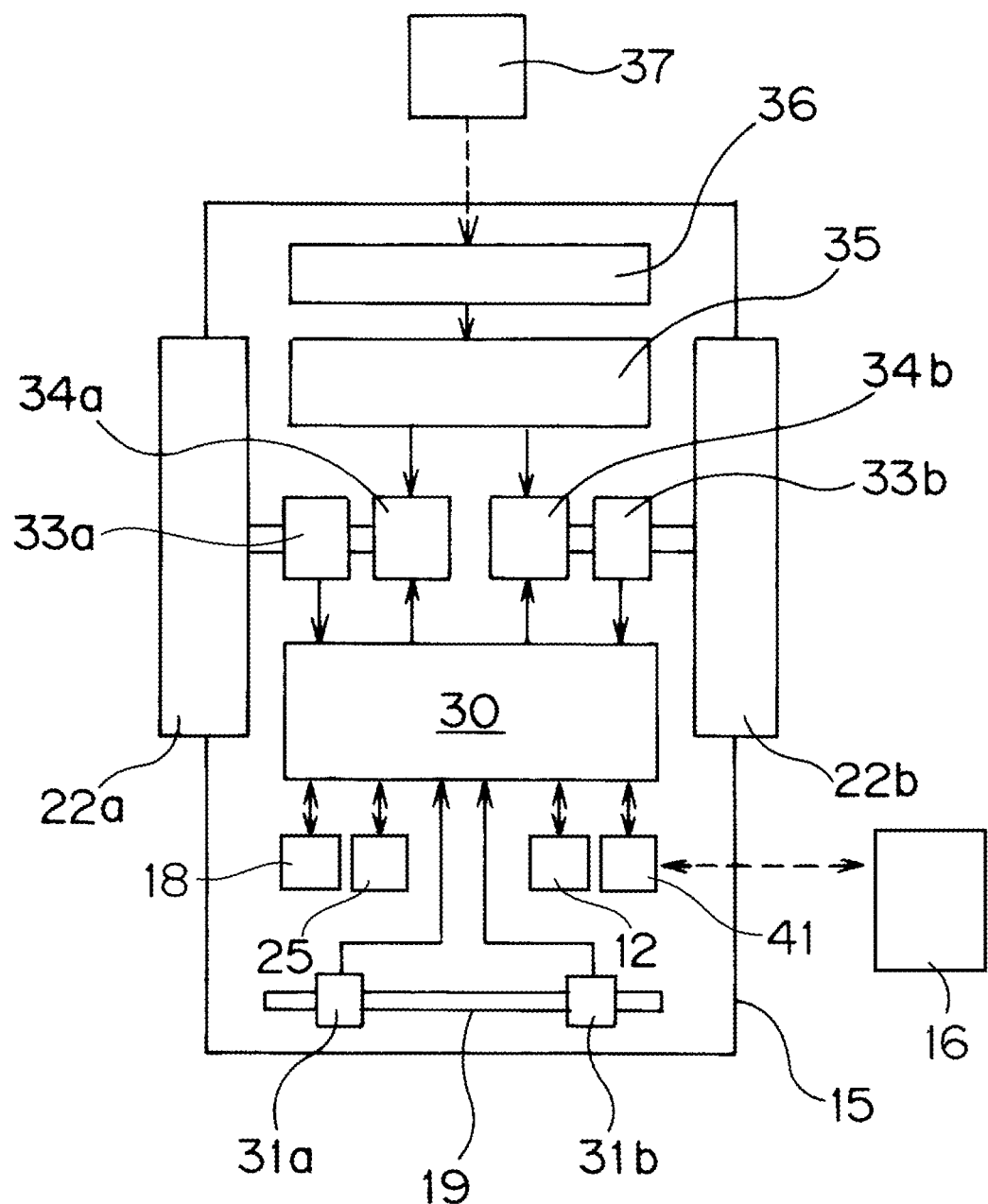
FIG. 3 is a circuit diagram for explaining the main electric configuration of the mobile X-ray imaging apparatus according to the present invention.

FIG. 3 is a circuit diagram for explaining the main electric configuration of the mobile X-ray imaging apparatus according to the present invention.

This mobile X-ray imaging apparatus is provided with a control unit 30 for controlling the entire apparatus within the carriage 15. Further, the mobile X-ray imaging apparatus is provided with a battery 35 within the carriage 15. The battery 35 is connectable to a charging station 37 with a commercial power supply via a charging circuit 36, and the battery 35 can be charged by connecting a power cord provided on the carriage 15 to the outlet of the charging station 37.

The right rear wheel 22a of the pair of rear wheels 22 for driving the carriage 15 is connected to a driving motor 34a via an encoder 33a. Similarly, the left rear wheel 22b is connected to a driving motor 34b via an encoder 33b. The encoder 33a and 33b detects the revolution of the rear wheel 22a and 22b. The encoder 33a and 33b and the driving motor 34a and 34b are connected to the control unit 30, and the control unit 30 transmits the rotational control signal of the driving motor 34a and 34b based on the rotational speed of the rear wheel 22a and 22b detected by the encoder 33a and 33b.

A pair of sensors 31a and 31b for detecting the operating force applied to the operation handle 19 is provided in the vicinity of the left and right ends of the operation handle 19. The sensor 31a and 31b has a configuration in which a lever is provided between pressure sensors arranged in the front-rear direction to detect the forward or rearward operating force applied to the vicinity of the right end or the left end of the operation handle 19 by an operator.

The control unit 30 controls the rotations of the pair of rear wheels 22a and 22b based on the signals of these sensors 31a and 31b. That is, when the sensor 31a near the right end of the operation handle 19 detects the forward operating force, the control unit 30 transmits a signal for rotating the rear wheel 22a forward to the driving motor 34a, and when the sensor 31a near the right end of the operation handle 19 detects the backward operating force, the control unit 30 transmits a signal for rotating the rear wheel 22a backward to the driving motor 34a. Similarly, when the sensor 31b near the left end of the operation handle 19 detects the forward operating force, the control unit 30 transmits a signal for rotating the rear wheel 22b forward to the driving motor 34b, and when the sensor 31b near the left end of the operation handle 19 detects the backward operating force, the control unit 30 transmits a signal for rotating the rear wheel 22b backward to the driving motor 34b. The signal from the control unit 30 at this time is such that the rotational speed of each driving motor 34a and 34b is proportional to the magnitude of the operating force to the operation handle 19. Therefore, the mobile X-ray imaging apparatus travels in the operating direction in accordance with the operating force applied to the operation handle 19 by the operator. The number of rotations and the rotational direction of the rear wheel 22a and 22b are detected by the encoder 33a and 33b.

As shown in the figure, a transmitting and receiving unit 41 for transmitting and receiving data wirelessly to and from the X-ray detector 16 is connected to the control unit 30. The control unit 30 is connected to a touch panel type liquid crystal display 25 which is provided on the upper surface of the carriage 15 and functions as a display unit and an input/output unit. The control unit 30 is connected to the collimator 12 described above, and transmits and receives control signals to and from the collimator 12, as will be described later. Further, this control unit 30 is connected to the above-mentioned fixed portion 18, and detects that the apparatus has become a traveling mode for traveling the carriage 15 when the pin 23 provided on the lower surface of the arm 13 is accommodated in the hole portion formed in the fixed portion 18.

The above-mentioned X-ray detector 16 and the liquid crystal display 25 constitute a part of the digital imaging mechanism of the present invention. This digital imaging mechanism becomes an imaging mode only when imaging is actually performed and becomes a power saving mode (sleep mode) that minimizes the power consumption in other states. The control unit 30 constantly monitors whether or not the digital imaging mechanism including the X-ray detector 16 and the liquid crystal display 25 has become the imaging mode.

Figure 4:
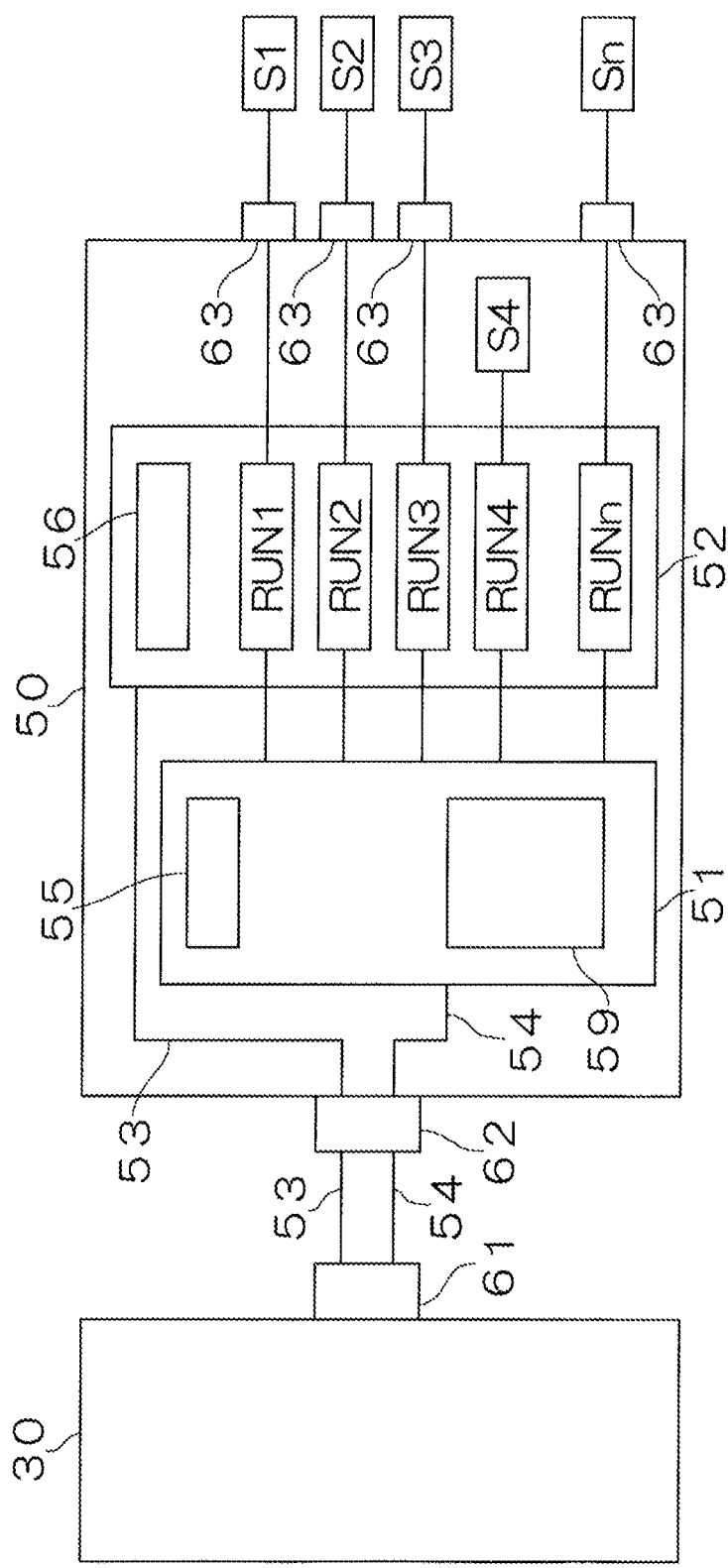
FIG. 4 is a block diagram showing, together with a control unit 30 provided in a carriage 15, a control board 50 and a plurality of sensors S1, S2, S3, S4, . . . , Sn provided in a collimator 12.

FIG. 4 is a block diagram showing a control board 50 and a plurality of sensors S1, S2, S3, S4, . . . , Sn, provided in the collimator 12, together with the control unit 30 provided in the carriage 15.

The control board 50 provided in the collimator 12 is provided with a power supply circuit 52 capable of individually supplying electric power to a plurality of sensors S1, S2, S3, S4, . . . , Sn, and a control circuit 51 for instructing supply and suspension of power supply from the power supply circuit 52 to a plurality of sensors S1, S2, S3, S4, . . . , Sn. The control board 50 is connected to the control unit 30 provided in the carriage 15 via a connector 62, a power supply line 53, a communication line 54, and a connector 61. The control unit 30 transmits a control signal to the control circuit 51 in the control board 50 to selectively supply electric power to the plurality of sensors S1, S2, S3, S4, . . . , Sn from the power supply circuit 52.

The control circuit 51 includes a processor 59. The processor 59 controls the power supply from the power supply circuit 52 to the plurality of sensors S1, S2, S3, S4, . . . , Sn in response to the command from the control unit 30. Note that instead of the processor 59, a logic circuit, such as, e.g., a programmable logic circuit, may be used.

The power supply circuit 52 is provided with a plurality of output command pins RUN1, RUN2, RUN3, RUN4, . . . , RUNn for supplying electric power to the plurality of sensors S1, S2, S3, S4, . . . , Sn. Of the plurality of sensors S1, S2, S3, S4, . . . , Sn, the sensor S1 is an acceleration sensor for measuring acceleration of the collimator 12. The sensor S2 is an opening-degree sensor for detecting the opening-degree of the collimator leaf in the collimator 12. The sensor S3 is a distance sensor for detecting the distance between the X-ray tube 11 and a subject. Note that the sensor S4 out of the plurality of sensors S1, S2, S3, S4, . . . , Sn is arranged directly on the control board 50. The sensors other than the sensor S4 out of the plurality of sensors S1, S2, S3, S4, . . . , Sn are arranged at any positions of the collimator 12, and are connected to the power supply circuit 52 via the connectors 63. As the plurality of sensors S1, S2, S3, S4, . . . , Sn, various types of sensors can be used to detect information for operation of the mobile X-ray imaging apparatus, such as information for X-ray imaging.

The control circuit 51 is provided with a timer 55 for measuring the time since the power supply circuit 52 initiated the power supply to the plurality of sensors S1, S2, S3, S4, . . . , Sn. The power supply circuit 52 is provided with a stability determination unit 56 for determining whether or not the power supply from the power supply circuit 52 to the plurality of sensors S1, S2, S3, S4, . . . , Sn has stabilized.

Next, a first embodiment of the supply control operation for supplying electric power to the plurality of sensors S1, S2, S3, S4, ..., Sn in the mobile X-ray imaging apparatus having the above-described configuration will be described.

In the electric power supply operation according to this first embodiment, when the control unit 30 detects that the pin 23 provided on the lower surface of the arm 13 is accommodated in the hole portion formed in the fixed portion 18 and therefore the apparatus becomes a traveling mode for driving the carriage 15, the control unit 30 supplies electric power to the sensor required to perform constant monitoring out of the plurality of sensors S1, S2, S3, S4, ..., Sn, and stops power supply to other sensors used when performing X-ray imaging. More specifically, the control unit 30 stops the power supply from the power supply circuit 52 to the opening-degree sensor S2 of the collimator leaf and the distance sensor S3 for detecting the distance between the X-ray tube 11 and the subject. On the other hand, the control unit 30 stops the power supply to the acceleration sensor S1, and supplies electric power to the acceleration sensor S1 for measuring the acceleration of the collimator 12 from the power supply circuit 52.

On the other hand, when the control unit 30 determines that the pin 23 provided on the lower surface of the arm 13 is not accommodated in the hole formed in the fixed portion 18 and the apparatus is not in a traveling mode for traveling the carriage 15, the control unit 30 controls such that electric power is supplied to all of the plurality of sensors S1, S2, S3, S4, ..., Sn, which are both the sensor required to perform constant monitoring and the sensor used when performing X-ray imaging. More specifically, electric power is supplied to all of the acceleration sensor S1, the opening-degree sensor S2, and the distance sensor S3.

By adopting such a configuration, electric power is constantly supplied to the acceleration sensor S1 required to perform constant monitoring, and in the traveling mode, the power supply to the opening-degree sensor S2 and the distance sensor S3, which are used when performing X-ray imaging, is stopped, so that power consumption can be reduced.

Then, the control unit 30 allows the acquisition of the detection values from the plurality of sensors S1, S2, S3, S4, ..., Sn from the time measurement values of the timer 55 provided in the control circuit 51 at the time when the time from the initiation of the power supply from the power supply circuit 52 to the plurality of sensors S1, S2, S3, S4, ..., Sn has elapsed a preset set time. With this, it becomes possible to prevent the acquisition of incorrect detection values prior to the stabilization of sensor outputs.

Further, the control unit 30 allows the acquisition of the detection values from the plurality of sensors S1, S2, S3, S4, ..., Sn from the measurement values of the stability determination unit 56 provided in the power supply circuit 52 at the time when the power supply from the power supply circuit 52 to the plurality of sensors S1, S2, S3, S4, ..., Sn has stabilized. With this, it becomes possible to prevent the acquisition of incorrect detection values prior to the stabilization of electric power.

Note that in this first embodiment, incorrect detection values are prevented from being acquired by using the timer 55 and the stability determination unit 56, but incorrect detection values may be prevented from being acquired by using either the timer 55 or the stability determination unit 56.

Also note that in the above-described first embodiment, it is detected that the apparatus has become the traveling mode for traveling the carriage 15 when the pin 23 provided on the lower surface of the arm 13 is accommodated in the hole formed in the fixed portion 18. However, it may be configured to detect that the apparatus has become the traveling mode for traveling the carriage 15 when the control unit 30 detects that the rear wheels 22a and 22b are rotating based on the output values of the encoders 33a and 33b.

Next, a second embodiment of the supply control operation for supplying electric power to the plurality of sensors S1, S2, S3, S4, ..., Sn will be described.

In the electric power supply operation according to the second embodiment, the control unit 30 is constantly monitoring whether or not the digital imaging mechanism provided with the X-ray detector 16 and the liquid crystal display 25 has become the imaging mode. Then, when this digital imaging mechanism is not in the imaging mode, electric power is supplied to the sensor required to perform constant monitoring out of the plurality of sensors S1, S2, S3, S4, ..., Sn, and power supply to other sensors used when performing X-ray imaging is stopped. More specifically, the power supply from the power supply circuit 52 to the opening-degree sensor S2 of the collimator leaf and the distance sensor S3 for detecting the distance between the X-ray tube 11 and the subject is stopped. On the other hand, electric power is supplied to the acceleration sensor and electric power is supplied from the power supply circuit 52 to the acceleration sensor S1 for measuring the acceleration of the collimator 12.

On the other hand, when the digital imaging mechanism has become the imaging mode, electric power is supplied to all of the plurality of sensors S1, S2, S3, S4, ..., Sn, which are both the sensor required to perform constant monitoring and the sensors used when performing X-ray radiography. More specifically, electric power is supplied to all of the acceleration sensor S1, the opening-degree sensor S2, and the distance sensor S3.

By adopting such a configuration, power consumption can be reduced by constantly supplying electric power to the acceleration sensor S1 required to perform constant monitoring, and stopping power supply to the opening-degree sensor S2 and the distance sensor S3 used when performing X-ray imaging when it is not in the imaging mode.

Note that in this second embodiment, it is possible to prevent incorrect detection values from being acquired by using the timer 55 or the stability determination unit 56.

Also note that in the above-described embodiment, although power supply to the plurality of sensors S1, S2, S3, S4, ..., Sn is controlled by a single power supply circuit 52, a plurality of power supply circuits may be provided corresponding to the respective sensors S1, S2, S3, S4, ..., Sn.

Further note that in the above-described embodiment, a plurality of sensors S1, S2, S3, S4, ..., Sn is connected to the output command pins RUN1, RUN2, RUN3, RUN4, RUNn corresponding to the sensors S1, S2, S3, S4, ..., Sn. However, for the sensors having the same detection timing, power supply may be performed simultaneously by connecting the sensors to the same output command pin.

Further, in the above-described embodiment, the timer 55 is provided in the control circuit 51, but the timer 55 may be provided in the control unit 30.

DESCRIPTION OF SYMBOLS

11: X-ray tube
12: collimator
13: arm
14: support post
15: carriage
16: X-ray detector
18: fixed portion 23: pin
25: liquid crystal display
30: control unit
35: battery
50: control board
51: control circuit
52: power supply circuit
53: power supply line
54: communication line
55: timer
56: stability determination unit
59: processor
S1: acceleration sensor
S2: opening-degree sensor
S3: distance sensor

The invention claimed is:

1. A mobile X-ray imaging apparatus equipped with an X-ray tube for emitting X-rays to a subject, a collimator for limiting an irradiation field of X-rays emitted from the X-ray tube to the subject, a carriage having wheels, a support mechanism mounted on the carriage for supporting the X-ray tube and the collimator, and a battery mounted on the carriage, the mobile X-ray imaging apparatus comprising:
    a plurality of sensors amounted on the collimator,
        a control board provided with a power supply circuit capable of individually supplying electric power to the plurality of sensors and a control circuit for instructing power supply and power supply stop from the power supply circuit to the plurality of sensors, and provided in the control board; and
        a control unit mounted on the carriage to control power supply to the plurality of sensors by transmitting a control signal to the control circuit in the control board.

2. The mobile X-ray imaging apparatus as recited in claim 1, further comprising:
    a traveling mode detection means configured to detect whether or not the apparatus is in a traveling mode for traveling the carriage,
    wherein the control unit switches a power supply state to the plurality of sensors based on a detection result of the traveling mode detection means.

3. The mobile X-ray imaging apparatus as recited in claim 2,
    wherein the traveling mode detection means detects that the apparatus is in the traveling mode by detecting that the support mechanism is positioned at a fixed position which is a position to be placed when the carriage is traveled.

4. The mobile X-ray imaging apparatus as recited in claim 2,
    wherein the plurality of sensors includes an opening-degree sensor for detecting an opening-degree of a collimator leaf in the collimator, a distance sensor for detecting an imaging distance between the X-ray tube and the subject and an acceleration sensor for detecting acceleration of the collimator, and
    wherein the control unit is configured to supply power to the opening-degree sensor, the distance sensor, and the acceleration sensor from the power supply circuit when the carriage is not in the traveling mode and supply power to the acceleration sensor from the power supply circuit when the carriage is in the traveling mode.

5. The mobile X-ray imaging apparatus as recited in claim 1, further comprising:
    a digital imaging mechanism including an X-ray detector for imaging an X-ray image by detecting X-rays emitted from the X-ray tube and passed through the subject and a display unit for displaying the X-ray image captured by the X-ray detector,
    wherein the control unit switches a power supply state to the plurality of sensors based on whether or not the digital imaging mechanism has become an imaging mode.

6. The mobile X-ray imaging apparatus as recited in claim 5,
    wherein the plurality of sensors includes an opening-degree sensor for detecting an opening-degree of a collimator leaf in the collimator, a distance sensor for detecting an imaging distance between the X-ray tube and the subject, and an acceleration sensor for detecting acceleration of the collimator, and
    wherein the control unit supplies electric power from the power supply circuit to the opening-degree sensor, the distance sensor, and the acceleration sensor when the digital imaging mechanism is in the imaging mode and supplies electric power from the power supply circuit to the acceleration sensor when the digital imaging mechanism is not in the imaging mode.

7. The mobile X-ray imaging apparatus as recited in claim 1, further comprising:
    a timer configured to measure a time since power supply to the plurality of sensors from the power supply circuit is initiated,
    wherein the control unit acquires detection values of the sensors after the timer measures that a set time has elapsed since electric power supply to the plurality of sensors stabilized.

8. The mobile X-ray imaging apparatus as recited in claim 1, further comprising:
    a stability determination unit configured to determine whether or not electric power supplied from the power supply circuit to the plurality of sensors has become stable,
    wherein the control unit acquires detection values of the sensors after electric power supplied to the plurality of sensors has stabilized.

* * * * *